(12) United States Patent
Sasai

(10) Patent No.: US 11,246,209 B2
(45) Date of Patent: Feb. 8, 2022

(54) RADIATION TREATMENT APPARATUS

(71) Applicant: SUMITOMO HEAVY INDUSTRIES, LTD., Tokyo (JP)

(72) Inventor: Kenzo Sasai, Tokyo (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 0 days.

(21) Appl. No.: 17/020,035

(22) Filed: Sep. 14, 2020

(65) Prior Publication Data

US 2021/0084744 A1    Mar. 18, 2021

(30) Foreign Application Priority Data

Sep. 17, 2019  (JP) .............................. JP2019-168554

(51) Int. Cl.
| | | |
|---|---|---|
| *H05H 7/10* | (2006.01) | |
| *A61N 5/10* | (2006.01) | |
| *H05H 7/02* | (2006.01) | |
| *H05H 5/00* | (2006.01) | |

(52) U.S. Cl.
CPC ............ *H05H 7/10* (2013.01); *A61N 5/1048* (2013.01); *A61N 5/1077* (2013.01); *H05H 5/00* (2013.01); *H05H 7/02* (2013.01); *A61N 2005/1087* (2013.01)

(58) Field of Classification Search
None
See application file for complete search history.

(56) References Cited

U.S. PATENT DOCUMENTS

| | | | | |
|---|---|---|---|---|
| 7,807,982 B2 * | 10/2010 | Nishiuchi | ............ | A61N 5/1043 250/492.2 |
| 8,586,942 B2 * | 11/2013 | Honda | ................ | A61N 5/1071 250/397 |
| 8,637,837 B2 * | 1/2014 | Natori | ................. | A61N 5/1043 250/492.1 |
| 8,841,866 B2 * | 9/2014 | Balakin | .................... | G21K 1/14 315/500 |

(Continued)

FOREIGN PATENT DOCUMENTS

JP      2016-191621 A     11/2016

*Primary Examiner* — Amy Cohen Johnson
*Assistant Examiner* — Srinivas Sathiraju
(74) *Attorney, Agent, or Firm* — Michael Best & Friedrich LLP

(57) ABSTRACT

A radiation treatment apparatus includes an accelerator that emits a charged particle beam, a time measurement unit that measures an emission time of the charged particle beam of the accelerator, a first control unit that controls the accelerator based on the emission time measured by the time measurement unit, and an emission determination unit that determines whether or not the accelerator is emitting the charged particle beam while the first control unit is controlling the accelerator. The time measurement unit adds a time, for which a result of a determination performed by the emission determination unit is that the accelerator is emitting the charged particle beam, to the emission time and does not add a time, for which the result of the determination performed by the emission determination unit is that the accelerator is not emitting the charged particle beam, to the emission time.

7 Claims, 3 Drawing Sheets

(56) References Cited

U.S. PATENT DOCUMENTS

| | | | | |
|---|---|---|---|---|
| 8,901,509 B2* | 12/2014 | Balakin | ................. | G21K 1/087 |
| | | | | 250/396 R |
| 8,957,396 B2* | 2/2015 | Balakin | ................... | H05H 7/10 |
| | | | | 250/492.3 |
| 9,044,600 B2* | 6/2015 | Balakin | .................. | H05H 13/04 |
| 9,056,199 B2* | 6/2015 | Balakin | ............... | A61B 6/0421 |
| 9,061,143 B2* | 6/2015 | Sasai | ....................... | G21K 1/10 |
| 9,649,510 B2* | 5/2017 | Balakin | ................. | A61N 5/107 |
| 11,000,705 B2* | 5/2021 | Lee | ........................ | A61B 6/03 |
| 2006/0022152 A1* | 2/2006 | Natori | .................... | A61N 5/10 |
| | | | | 250/493.1 |
| 2007/0228304 A1* | 10/2007 | Nishiuchi | ................ | G21K 1/10 |
| | | | | 250/505.1 |
| 2009/0283704 A1* | 11/2009 | Nishiuchi | ................ | H05H 7/10 |
| | | | | 250/492.3 |
| 2011/0073778 A1* | 3/2011 | Natori | .................. | A61N 5/1043 |
| | | | | 250/492.3 |
| 2012/0211667 A1* | 8/2012 | Iwata | .................. | A61N 5/1043 |
| | | | | 250/396 ML |
| 2012/0228521 A1* | 9/2012 | Honda | ................. | A61N 5/1043 |
| | | | | 250/492.3 |
| 2013/0023716 A1* | 1/2013 | Thomas | ............... | A61N 5/1071 |
| | | | | 600/1 |
| 2013/0253845 A1* | 9/2013 | Iwata | ...................... | A61B 5/48 |
| | | | | 702/19 |
| 2014/0252227 A1* | 9/2014 | Sasai | ...................... | G21K 1/046 |
| | | | | 250/307 |
| 2017/0017232 A1* | 1/2017 | Nishiuchi | .......... | G05B 23/0256 |
| 2019/0018154 A1* | 1/2019 | Olcott | .................... | G01T 7/005 |

* cited by examiner

RADIATION TREATMENT APPARATUS

RELATED APPLICATIONS

The content of Japanese Patent Application No. 2019-168554, on the basis of which priority benefits are claimed in an accompanying application data sheet, is in its entirety incorporated herein by reference.

BACKGROUND

Technical Field

A Certain embodiment of the present invention relates to a radiation treatment apparatus.

Description of Related Art

In the related art, as an apparatus used for a therapy in which irradiation with radiant rays is performed to kill cancer cells, an apparatus as described in the related art is known. A neutron capture therapy apparatus as described in the related art is used in a neutron capture therapy in which irradiation with neutrons is performed to kill cancer cells. The neutron capture therapy apparatus includes a first current measurement unit that measures the current of a charged particle beam, a second current measurement unit that measures the current of the charged particle beam at a position downstream of the first current measurement unit, and a control unit that controls an accelerator based on measured current values. The neutron capture therapy apparatus measures a decrease in current value by means of the first current measurement unit and the second current measurement unit during transportation of the charged particle beam and performs control in accordance with the decrease in current value.

SUMMARY

According to an embodiment of the present invention, there is provided a radiation treatment apparatus including an accelerator that emits a charged particle beam, a time measurement unit that measures an emission time of the charged particle beam of the accelerator, a first control unit that controls the accelerator based on the emission time measured by the time measurement unit, and an emission determination unit that determines whether or not the accelerator is emitting the charged particle beam while the first control unit is controlling the accelerator, in which the time measurement unit adds a time, for which a result of a determination performed by the emission determination unit is that the accelerator is emitting the charged particle beam, to the emission time of the charged particle beam of the accelerator and does not add a time, for which the result of the determination performed by the emission determination unit is that the accelerator is not emitting the charged particle beam, to the emission time of the charged particle beam of the accelerator.

DETAILED DESCRIPTION

Figure 1:
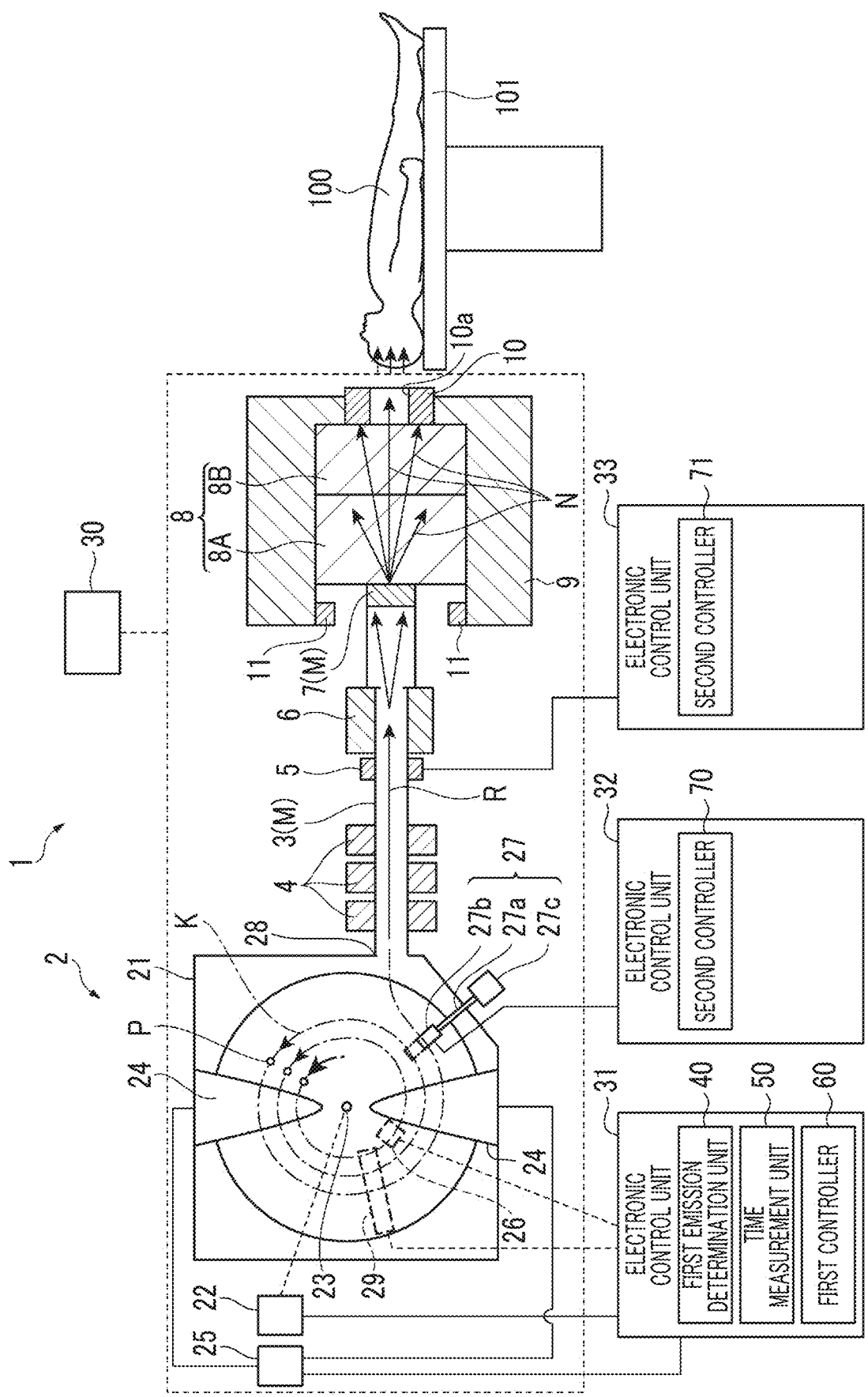
FIG. 1 is a schematic view showing a neutron capture therapy system which is an example of a radiation treatment apparatus according to an embodiment.

In the case of a neutron capture therapy apparatus as described in the related art, a controller of an accelerator by using a control system including a timer independent of a control unit is also conceivable in addition to a controller of the accelerator based on a current value by using the control unit. The control system including the timer controls the accelerator to end a radiation treatment in a case where a time that has elapsed from the start of measurement reaches an irradiation completion time determined in advance. Therefore, in a case where irradiation with a charged particle beam that does not fit the original treatment plan is performed temporarily (for example, temporary stoppage of emission), the control system including the timer may end the irradiation with the charged particle beam without following a treatment plan updated by the control unit.

It is desirable to provide a radiation treatment apparatus with which it is possible to end emission of a charged particle beam at an appropriate timing.

The radiation treatment apparatus includes a time measurement unit that adds a time, for which the result of a determination performed by an emission determination unit is that an accelerator is emitting a charged particle beam, to the emission time of the charged particle beam and a first control unit that controls the accelerator based on the emission time measured by the time measurement unit. According to such a configuration, the time, for which the result of the determination is that the accelerator is not emitting the charged particle beam, is not added to the emission time and thus the first control unit can perform control in accordance with the state of emission of the charged particle beam. Accordingly, with the radiation treatment apparatus, it is possible to end emission of the charged particle beam at an appropriate timing.

In the embodiment, the emission determination unit may determine whether or not the charged particle beam is being emitted based on information indicating a state of generation of the charged particle beam in the accelerator. The time measurement unit can measure the emission time of the charged particle beam through a determination that is performed based on information indicating the state of generation of the charged particle beam in the emission determination unit. Accordingly, with the radiation treatment apparatus, it is possible to appropriately measure the emission time of the charged particle beam.

In the embodiment, the accelerator may include a generation source that generates a charged particle and the emission determination unit may determine whether or not the accelerator is emitting the charged particle beam based on information indicating a state of generation of the charged particle at the generation source. The time measurement unit can measure the emission time of the charged particle beam through a determination that is performed based on the information indicating the state of generation of the charged particle beam at the generation source in the emission determination unit. Accordingly, with the radiation treatment apparatus, it is possible to appropriately measure the emission time of the charged particle beam in the accelerator.

In the embodiment, the accelerator may include a stopper that is provided on a trajectory of the charged particle beam and controls passage and blockage of the charged particle beam by being opened and closed and the emission determination unit may determine whether or not the accelerator is emitting the charged particle beam based on information indicating an opening and closing state of the stopper. The time measurement unit can measure the emission time of the charged particle beam through a determination that is performed based on the information indicating the opening and closing state of the stopper in the emission determination unit. Accordingly, with the radiation treatment apparatus, it is possible to appropriately measure the emission time of the charged particle beam in the accelerator based on the information indicating the opening and closing state of the stopper in the accelerator.

In the embodiment, the accelerator may include a signal source that outputs high-frequency electric power and the emission determination unit may determine whether or not the accelerator is emitting the charged particle beam based on information indicating a state of the high-frequency electric power. The time measurement unit can measure the emission time of the charged particle beam through a determination that is performed based on the information indicating the state of the high-frequency electric power of the signal source in the emission determination unit. Accordingly, with the radiation treatment apparatus, it is possible to appropriately measure the emission time of the charged particle beam in the accelerator based on the information indicating the state of the high-frequency electric power of the signal source in the accelerator.

The radiation treatment apparatus may further include a plurality of charged particle beam measurement units that are provided in a beam path of the charged particle beam and measure a state of the charged particle beam and a plurality of second control units that control the accelerator based on a result of measurement performed by the plurality of charged particle beam measurement units and the first control unit and the plurality of second control units may control the accelerator independently of each other. In this case, the first control unit and the plurality of second control units can control the accelerator based on the emission time in the time measurement unit and the result of measurement in the plurality of signal measurement units. Since the first control unit and the plurality of second control units are independent of each other, with the radiation treatment apparatus, it is possible to end emission of the charged particle beam at an appropriate timing based on a plurality of conditions.

In the embodiment, the accelerator may include an interlock that regulates emission of the charged particle beam and the time measurement unit may continue measurement of the emission time in a case where the interlock does not regulate the emission of the charged particle beam and end the measurement of the emission time in a case where the interlock regulates the emission of the charged particle beam. In a case where the interlock does not regulate the emission of the charged particle beam, even when the emission of the charged particle beam is stopped, the stoppage can be regarded as temporary stoppage where automatic restoration is possible, for example. Therefore, the time measurement unit can continue the measurement of the emission time and can handle the above-described temporary stoppage as a time not to be added to the emission time. Meanwhile, in a case where the interlock regulates the emission of the charged particle beam, it may take time to terminate the regulation. Therefore, the time measurement unit ends the measurement of the emission time in a case where the interlock regulates the emission of the charged particle beam. Accordingly, it is possible to restrain the time measurement unit from performing the measurement for an unnecessarily long time.

According to the embodiment of the invention, it is possible to provide a radiation treatment apparatus with which it is possible to end emission of a charged particle beam at an appropriate timing.

Hereinafter, a preferred embodiment of the invention will be described in detail with reference to the drawings.

A radiation treatment apparatus is an apparatus used for a cancer treatment or the like through radiotherapy. The radiation treatment apparatus is, for example, a charged particle beam treatment apparatus, a neutron capture therapy apparatus, or the like. The charged particle beam treatment apparatus accelerates charged particles generated by an ion source unit and emits the charged particles in the form of a charged particle beam. The charged particle beam is a particle beam obtained by accelerating charged particles at a high speed and examples thereof include a proton beam, a neutron ray, a heavy particle (heavy ion) beam, and a particle beam. In addition, the neutron capture therapy apparatus generates a neutron ray by irradiating a target with a charged particle beam. The radiation treatment apparatus irradiates a tumor (irradiation target) in the body of a patient with a charged particle beam or a neutron ray.

In the embodiment, description will be made using a neutron capture therapy apparatus, which is an example of the radiation treatment apparatus. A neutron capture therapy apparatus 1 as shown in FIG. 1, which is an example of the radiation treatment apparatus, is an apparatus for cancer treatment in which a boron neutron capture therapy (BNCT) is used. In the neutron capture therapy apparatus 1, for example, a tumor of a patient (irradiation target) 100 to which boron (10B) is administered is irradiated with a neutron ray N. The patient 100 is disposed on an examination table 101.

The neutron capture therapy apparatus 1 includes an accelerator 2. The accelerator 2 is a device that accelerates charged particles such as negative ions, forms a charged particle beam K, and emits a charged particle beam R having a pre-set energy. In the case of the embodiment, a cyclotron has been adopted as the accelerator 2. Note that, as the accelerator 2, other accelerators such as a circular accelerator (for example, synchrotron), a linear accelerator (for example, linac), or an electrostatic accelerator may also be used instead of the cyclotron. In the embodiment, the charged particle beam K and the charged particle beam R may be composed of different charged particles and maybe composed of the same charged particles. In the embodiment, the charged particle beam K is a beam generated by means of accelerated negative ions P and the charged particle beam R is a proton beam generated by tearing electrical charges off the negative ions P constituting the charged particle beam K. The accelerator 2 has an ability to generate the charged particle beam R of 60 kW power (=30 MeV×2 mA), of which the beam radius is 40 mm.

Specifically, the accelerator 2 includes a vacuum chamber 21 in which the negative ions P orbit, an ion source unit 22 (example of generation source) that generates the negative ions P, and an ion supply port 23 through which negative ions are supplied to the vacuum chamber 21 from the ion source unit 22. In addition, the accelerator 2 includes a pair of acceleration electrodes 24 disposed between a pair of magnetic poles (not shown), a signal source 25 that supplies high-frequency electric power to the acceleration electrodes 24, and a stopper 26 that captures the negative ions P. Furthermore, the accelerator 2 includes a foil stripper 27 that tears electrons off the negative ions P, an emission port 28 for extraction of a proton of which the trajectory has been changed by the foil stripper 27, and an interlock 29.

Negative ions are supplied into the vacuum chamber 21 and accelerated negative ions are emitted from the vacuum chamber 21. The vacuum chamber 21 is provided with an exhaust port (not shown) for evacuation. A vacuum pump (not shown) is connected to the exhaust port. The inside of the vacuum chamber 21 is made vacuum by the vacuum pump. In the vacuum chamber 21, a pair of magnetic poles (not shown) surrounded by an annular coil is disposed such that the magnetic poles face each other. The shape of each of the pair of magnetic poles is columnar. Disc surfaces of the pair of magnetic poles face each other. When a current is supplied to the coil surrounding the magnetic poles, a magnetic flux in a direction from one magnetic pole to the other magnetic pole is generated. That is, in the vacuum chamber 21, an electromagnet is formed by the pair of magnetic poles surrounded by the annular coil. The inside of the vacuum chamber 21 has a columnar shape with a disk serving as an upper surface or a bottom surface thereof, the disk having the approximately same diameter as the disk surfaces of the pair of magnetic poles.

The vacuum chamber 21 is provided with the ion supply port 23 through which the negative ions P generated by the ion source unit 22 are supplied into the vacuum chamber 21. The ion source unit 22 is a device that generates the negative ions P by performing arc discharge in a raw material such as a hydrogen gas. The ion source unit 22 may be disposed outside the accelerator 2 and may be disposed inside the accelerator 2. The negative ions P generated by the ion source unit 22 are supplied to be drawn into the vacuum chamber 21 via the ion supply port 23.

The ion source unit 22 includes an ion source monitor (not shown). The ion source monitor detects a signal of a current value, a voltage value, or the like used for arc discharge in real time. Examples of the ion source monitor include an ammeter, a voltmeter, a flowmeter, and a Faraday cup. The ion source monitor outputs the result of detection to an ion source determination unit of an emission determination unit 40, which will be described later, as information (example of information indicating state of generation of charged particle beam) indicating the state of generation of the negative ions P in the ion source unit 22. Note that, such information may be referred to as ion source information.

The acceleration electrodes 24 to which a high-frequency voltage is applied cause the negative ions P supplied into the vacuum chamber 21 to accelerate while orbiting. The acceleration electrodes 24 are connected to the signal source 25 that outputs high-frequency electric power. The acceleration electrodes 24 are operated by high-frequency electric power supplied from the signal source 25 and accelerate the negative ions P. The negative ions P accelerated by the acceleration electrodes 24 gradually increase in energy. As the energy increases, the radius of gyration of the negative ions P increases and an orbit as drawn at the time of a spiral motion is drawn. At this time, the accelerated negative ions P form the charged particle beam K.

The signal source 25 includes a signal source monitor (not shown). The signal source monitor detects a signal of high-frequency electric power, the current value of the high-frequency electric power, or the voltage value of the high-frequency electric power in real time in a case where the high-frequency electric power is output. Examples of the signal source monitor include an ammeter, a voltmeter, and a thermometer. The signal source monitor outputs the result of detection to a signal source determination unit of the emission determination unit 40, which will be described later, as information (example of information indicating state of generation of charged particle beam) indicating the state of generation of high-frequency electric power. Note that, such information may be referred to as high-frequency electric power information.

The stopper 26 is provided on the trajectory of the charged particle beam K in the vacuum chamber 21 and controls passage and blockage of the charged particle beam K by being opened and closed. That is, in a case where the trajectory of the charged particle beam K is opened by the stopper 26, the stopper 26 allows the charged particle beam K to pass by the stopper 26. In a case where the trajectory of the charged particle beam K is closed by the stopper 26, the stopper 26 blocks the charged particle beam K. The stopper 26 is, for example, a Faraday cup. In a case where the trajectory of the charged particle beam K is closed by the stopper 26, the stopper 26 captures the negative ions P that are supplied into the vacuum chamber 21 via the ion supply port 23, for example.

The stopper 26 includes a stopper monitor (not shown). The stopper monitor detects the opening and closing of the stopper 26 in real time. The stopper monitor acquires, for example, an opening and closing signal determined for each of the opening of the stopper 26 and the closing of the stopper 26. For example, in a state where the stopper 26 allows a charged particle beam to pass by the stopper 26, the stopper monitor acquires an opening and closing signal of "OFF". For example, in a state where the stopper 26 blocks a charged particle beam, the stopper monitor acquires an opening and closing signal of "ON". The stopper monitor outputs an opening and closing signal to a stopper determination unit of the emission determination unit 40, as information (example of information indicating state of generation of charged particle beam) indicating the opening and closing state of the stopper 26. Note that, such information may be referred to as opening and closing information.

The foil stripper 27 takes electrons from the negative ions P constituting the charged particle beam K and guides protons to the emission port 28. The foil stripper 27 includes a stripper drive shaft 27a that extends along a radial direction of the accelerator 2, a foil 27b that is provided at a tip end of the stripper drive shaft 27a, and a foil drive unit 27c that drives the stripper drive shaft 27a such that the stripper drive shaft 27a can move forward and backward along a radial direction of the pair of magnetic poles. The foil drive unit 27c includes a high-accuracy motor or the like and the stripper drive shaft 27a is caused to move forward and backward in units of $10^{-2}$ mm to $10^{-1}$ mm through driving control performed by the foil drive unit 27c. As a result, the foil 27b can move forward and backward to intersect the orbit of the negative ions P (charged particle beam K).

The foil 27b is formed of a carbon thin film, for example. When the foil 27b enters the orbit of the orbiting negative ions P (charged particle beam K) and comes into contact with the negative ions P, the foil 27b tears electrons off the negative ions P. The curvature of the orbit of protons (accelerated particles) that have been deprived of electrons and changed from negative charges to positive charges is inverted and the trajectory thereof is changed to a direction to the outside of the orbit. On the trajectory of the protons after the inversion, the emission port 28 for extraction of the protons from the inside of the vacuum chamber 21 is provided. That is, the vacuum chamber 21 is provided with the emission port 28 that is on the trajectory of the protons of which the trajectory is changed by the foil stripper 27. Therefore, the foil 27b takes electrons from the negative ions P to consequently guide the protons to the emission port 28. Accordingly, the charged particle beam R formed by the guided protons is emitted from the accelerator 2 via the emission port 28 from the foil stripper 27. Note that, the accelerator 2 further includes a magnetic flux adjustment unit that includes an air-core coil generating a magnetic flux in the vicinity of the foil 27*b*.

The foil stripper 27 measures the amount of electrons torn off the negative ions P (example of charged particle beam measurement unit). The measured amount of electrons (that is, charge, exposure radiation dose rate) is detected in real time. The foil stripper 27 outputs the result of detection to a second control unit 70, which will be described later. Note that, "dose rate" means a dose per unit time.

The interlock 29 controls emission of the charged particle beams K and R caused by the accelerator 2. That is, with the interlock 29 not operated, the accelerator 2 can emit the charged particle beam K and the charged particle beam R. The interlock 29 may be, for example, a hardware configuration provided in the ion source unit 22, the signal source 25, or the stopper 26, or at least one of a hardware configuration provided in the accelerator 2 and a software configuration. In a case where the interlock 29 is operated based on an instruction made by a system or based on an instruction made by an operator or the like, the interlock 29 prohibits the accelerator 2 from emitting the charged particle beams K and R. Ina case where the interlock 29 is operated and the interlock 29 prohibits the accelerator 2 from emitting the charged particle beams K and R, the neutron capture therapy apparatus 1 is not restored automatically. That is, in a case where the interlock 29 prohibits the accelerator 2 from emitting the charged particle beams K and R, the neutron capture therapy apparatus 1 does not irradiate the patient 100 with the neutron ray N as long as there is no intervention from the outside such as an operation or the like performed by the operator. For example, when a reset key of the interlock 29 is rotated by the operator, the interlock 29 is manually restored. In a case where the interlock 29 prohibits the charged particle beams K and R from being emitted, the interlock 29 outputs, to the emission determination unit 40, information indicating that automatic restoration is not possible.

The charged particle beam R emitted from the accelerator 2 is sent to a neutron ray generating unit M. The neutron ray generating unit M includes a beam duct 3 and a target 7. The charged particle beam R emitted from the accelerator 2 passes through the beam duct 3 and proceeds toward the target 7 disposed at an end portion of the beam duct 3. A plurality of quadrupole electromagnets 4, a current monitor 5 (example of charged particle beam measurement unit), and a scanning electromagnet 6 are provided along the beam duct 3. The plurality of quadrupole electromagnets 4 perform beam axis adjustment of the charged particle beam R by using, for example, electromagnets.

The current monitor 5 measures the current value (that is, charge, exposure radiation dose rate) of the charged particle beam R with which the target 7 is irradiated in real time (example of signal measurement unit). As the current monitor 5, a non-destructive DC current transformer (DCCT) which can perform current measurement without influencing the charged particle beam R is used. The current monitor 5 outputs the result of measurement to a second control unit 71 which will be described later.

Specifically, the current monitor 5 is provided immediately before the scanning electromagnet 6 at a position downstream of the quadrupole electromagnets 4 (on downstream side of charged particle beam R) in order to remove the influence of the quadrupole electromagnets 4, so that the current monitor 5 accurately measures the current value of the charged particle beam R with which the target 7 is irradiated. That is, since the scanning electromagnet 6 performs scanning such that the same part of the target 7 is not irradiated with the charged particle beam R at all times, the current monitor 5 needs to be large in order that the current monitor 5 is disposed downstream of the scanning electromagnet 6. On the other hand, when the current monitor 5 is provided upstream of the scanning electromagnet 6, the current monitor 5 can be reduced in size.

The scanning electromagnet 6 performs scanning with the charged particle beam R and controls irradiation of the target 7 with the charged particle beam R. The scanning electromagnet 6 controls the irradiation position of the charged particle beam R with respect to the target 7.

In addition, the neutron capture therapy apparatus 1 generates the neutron ray N by irradiating the target 7 with the charged particle beam R and emits the neutron ray N toward the patient 100. The neutron capture therapy apparatus 1 includes the target 7, a shield member 9, a deceleration member 8, a collimator 10, and a gamma ray detection unit 11.

In addition, the neutron capture therapy apparatus 1 includes a controller 30. The controller 30 is composed of a central processing unit (CPU), a read only memory (ROM), a random access memory (RAM), and the like and is an electronic control unit that comprehensively controls the neutron capture therapy apparatus 1. The controller 30 performs automatic restoration of the neutron capture therapy apparatus 1, for example.

When the target 7 is irradiated with the charged particle beam R, the neutron ray N is generated. Here, the target 7 is formed of, for example, beryllium (Be), lithium (Li), tantalum (Ta), or tungsten (W), and has a disc shape having a diameter of 160 mm, for example. Note that, the shape of the target 7 is not limited to the disc shape and may be another shape. In addition, the target 7 may not be in a solid state and may be in a liquid state.

The deceleration member 8 decelerates the energy of the neutron ray N generated by the target 7. The deceleration member 8 has a layered structure composed of a first deceleration member 8A that is mainly for deceleration of fast neutrons contained in the neutron ray N and a second deceleration member 8B that is mainly for deceleration of epithermal neutrons contained in the neutron ray N.

The shield member 9 blocks the generated neutron ray N and a gamma ray or the like generated due to the generation of the neutron ray N such that the rays are not released to the outside. The shield member 9 is provided to surround the deceleration member 8. An upper portion and a lower portion of the shield member 9 extend toward an upstream side of the charged particle beam R further than the deceleration member 8 and the gamma ray detection unit 11 is provided at each of the extension portions.

The collimator 10 shapes the irradiation field of the neutron ray N and includes an opening 10*a* through which the neutron ray N passes. The collimator 10 is a block-shaped member of which the center is provided with the opening 10*a*, for example.

The gamma ray detection unit 11 detects a gamma ray, which is generated from the neutron ray generating unit M due to irradiation with the charged particle beam R, in real time. As the gamma ray detection unit 11, a scintillator, an ionization chamber, and various other gamma ray detection devices can be adopted. In the embodiment, the gamma ray detection unit 11 is provided near the target 7 and closer to the upstream side of the charged particle beam R than the deceleration member 8.

The gamma ray detection unit 11 is disposed inward of the upper portion and the lower portion of the shield member 9 that extend to the upstream side of the charged particle beam R. Note that, the number of the gamma ray detection units 11 it not particularly limited and may be one or three or more. When three or more gamma ray detection units 11 are provided, the gamma ray detection units 11 can be provided at predetermined intervals such that the gamma ray detection units 11 surround the outer periphery of the target 7. The gamma ray detection unit 11 outputs the result of gamma ray detection to the controller 30, for example. A configuration in which no gamma ray detection unit 11 is provided may also be adopted.

The beam path of the charged particle beam R in the embodiment refers to a path from a point at which the charged particle beam R is generated and a point at which the patient 100 is irradiated. That is, the starting point of the beam path of the charged particle beam R is the foil stripper 27 in the accelerator 2 and the endpoint thereof is the patient 100. The beam path of the charged particle beam R refers to the inside of each of the accelerator 2, the beam duct 3, the target 7, the deceleration member 8, and the collimator 10. The endpoint of the beam path of the charged particle beam R may be the target 7.

The neutron capture therapy apparatus 1 includes an electronic control unit 31 that controls emission of the charged particle beam K in the accelerator 2. The electronic control unit 31 has the same configuration as the controller 30, for example. The electronic control unit 31 includes the emission determination unit 40, a time measurement unit 50, and a first control unit 60. Note that, the emission determination unit 40, the time measurement unit 50, and the first control unit 60 may be provided in electronic control units independent of each other without being included in one electronic control unit 31.

The emission determination unit 40 determines whether or not the accelerator 2 is emitting the charged particle beams K and R. The emission determination unit 40 determines whether or not the charged particle beams K and R are being emitted based on information indicating the state of generation of the charged particle beams K and R in the accelerator 2. The emission determination unit 40 includes the ion source determination unit that determines whether or not the accelerator 2 is emitting the charged particle beams K and R based on ion source information from the ion source monitor of the ion source unit 22. In addition, the emission determination unit 40 includes the signal source determination unit that determines whether or not the accelerator 2 is emitting the charged particle beams K and R based on high-frequency electric power information from the signal source monitor of the signal source 25. Furthermore, the emission determination unit 40 includes the stopper determination unit that determines whether or not the accelerator 2 is emitting the charged particle beams K and R based on opening and closing information from the stopper monitor of the stopper 26.

In a case where a determination is made using the ion source information from the ion source monitor of the ion source unit 22, the ion source determination unit of the emission determination unit 40 determines whether or not the accelerator 2 is emitting the charged particle beams K and R through comparison between an ion source threshold value, which is a threshold value determined in advance, and the ion source information. As the ion source threshold value, a current value, a voltage value, or the like is determined in accordance with a unit of the ion source information. In a case where the ion source information is lower than the ion source threshold value, the ion source determination unit of the emission determination unit 40 determines that power required at the time of generation of the negative ions P is not supplied to the ion source unit 22 and the accelerator 2 is not emitting the charged particle beams K and R at a predetermined output. That is, in a case where the ion source information is lower than the ion source threshold value, the ion source determination unit of the emission determination unit 40 determines that the accelerator 2 is not emitting the charged particle beams K and R. In a case where the ion source information is equal to or greater than the ion source threshold value, the ion source determination unit of the emission determination unit 40 determines that the accelerator 2 is emitting the charged particle beams K and R.

In a case where a determination is made using the high-frequency electric power information from the signal source monitor of the signal source 25, the signal source determination unit of the emission determination unit 40 determines whether or not the accelerator 2 is emitting the charged particle beams K and R through comparison between a signal source threshold value, which is a threshold value determined in advance, and the high-frequency electric power information. As the signal source threshold value, power a current value, a voltage value, or the like is determined in accordance with a unit of the high-frequency electric power information. In a case where the high-frequency electric power information is lower than the signal source threshold value, the signal source determination unit of the emission determination unit 40 determines that there is no supply of high-frequency electric power required for the acceleration electrodes 24 from the signal source 25 and the accelerator 2 is not emitting the charged particle beams K and R at a predetermined output. That is, in a case where the high-frequency electric power information is lower than the signal source threshold value, the signal source determination unit of the emission determination unit 40 determines that the accelerator 2 is not emitting the charged particle beams K and R. In a case where the high-frequency electric power information is equal to or greater than the signal source threshold value, the signal source determination unit of the emission determination unit 40 determines that the accelerator 2 is emitting the charged particle beams K and R.

Furthermore, in a case where a determination is made using the opening and closing information from the stopper monitor of the stopper 26, the stopper determination unit of the emission determination unit 40 determines whether or not the accelerator 2 is emitting the charged particle beams K and R in accordance with the contents of the opening and closing information. In a case where an opening and closing signal, which is the opening and closing information, is "ON", the stopper determination unit of the emission determination unit 40 determines that the negative ions P are captured or blocked by the stopper 26 and the accelerator 2 is not emitting the charged particle beams K and R at a predetermined output. That is, in a case where the opening and closing signal, which is the opening and closing information, is "ON", the stopper determination unit of the emission determination unit 40 determines that the accelerator 2 is not emitting the charged particle beams K and R. In a case where the opening and closing signal, which is the opening and closing information, is "OFF", the stopper determination unit of the emission determination unit 40 determines that the accelerator 2 is emitting the charged particle beams K and R.

In the emission determination unit 40, one or more determinations from among the determination based on the ion source information, the determination based on the high-frequency electric power information, and the determination based on the opening and closing information are performed. The emission determination unit 40 determines that the accelerator 2 is emitting the charged particle beams K and R in a case where the results of all the determinations performed are that the accelerator 2 is emitting the charged particle beams K and R. That is, the emission determination unit 40 determines that the accelerator 2 is not emitting the charged particle beams K and R in a case where the results of one or more determinations from among the plurality of determinations are that the accelerator 2 is not emitting the charged particle beams K and R. The emission determination unit 40 transmits the result of the determination to the time measurement unit 50.

Note that, in a case where the result of the above-described determination is that the charged particle beams K and R are not being emitted, the emission determination unit 40 may determine that the interlock 29 is prohibiting the accelerator 2 from emitting the charged particle beams K and R and automatic restoration is possible. The emission determination unit 40 may transmit the result of the determination to the time measurement unit 50. In addition, in a case where the result of the above-described determination is that the charged particle beams K and R are not being emitted, automatic restoration in which the neutron capture therapy apparatus 1 is automatically restored by the controller 30 is performed.

In a case where the ion source determination unit of the emission determination unit 40 determines that the ion source information is lower than the ion source threshold value, the controller 30 performs, for example, automatic restoration in which a current value or a voltage value used for arc discharge in the ion source unit 22 is raised to a predetermined value. In a case where the signal source determination unit of the emission determination unit 40 determines that the high-frequency electric power information is lower than the signal source threshold value, the controller 30 performs, for example, automatic restoration in which the high-frequency electric power, the current value of the high-frequency electric power, or the voltage value of the high-frequency electric power in the signal source 25 is raised to a predetermined value. In a case where the stopper determination unit of the emission determination unit 40 determines that the opening and closing signal in the opening and closing information is "ON", the controller 30 performs, for example, automatic restoration in which the cause of the operation of the stopper 26 is removed such that the stopper 26 allows the negative ions P to pass by.

The time measurement unit 50 measures the emission time of the charged particle beams K and R of the accelerator 2. The emission time is a time elapsing under a condition under which the emission determination unit 40 determines that the accelerator 2 is emitting the charged particle beams K and R. The emission time can be converted into a time for which the patient 100 is irradiated with the neutron ray N. The time measurement unit 50 adds a time, for which the result of the determination performed by the emission determination unit 40 is that the accelerator 2 is emitting the charged particle beams K and R, to the emission time of the charged particle beams K and R of the accelerator 2. The time measurement unit 50 does not add a time, for which the result of the determination performed by the emission determination unit 40 is that the accelerator 2 is not emitting the charged particle beams K and R, to the emission time of the charged particle beams K and R of the accelerator 2. In a case where the result of the determination performed by the emission determination unit 40 is not received, the time measurement unit 50 ends the measurement of the emission time.

The time measurement unit 50 continues the measurement of the emission time in a case where the interlock 29 does not regulate emission of the charged particle beams K and R. The time measurement unit 50 ends the measurement of the emission time in a case where the interlock 29 regulates emission of the charged particle beams K and R. The time measurement unit 50 may directly receive a signal relating to regulation of emission of the charged particle beams K and R which is performed by the interlock 29 and may receive the signal via the emission determination unit 40.

A case where the time measurement unit 50 receives a signal relating to regulation of emission of the charged particle beams K and R, which is performed by the interlock 29, via the emission determination unit 40 will be described. In a case where the interlock 29 is operated, the emission determination unit 40 receives information indicating that automatic restoration is not possible and the emission determination unit 40 determines that the automatic restoration is not possible. That is, in a case where the interlock 29 is operated, the emission determination unit 40 determines that the interlock 29 is prohibiting the accelerator 2 from emitting the charged particle beams K and R.

It will be assumed that one or more determinations from among the determination based on the ion source information, the determination based on the high-frequency electric power information, and the determination based on the opening and closing information have been performed. Even in a case where the results of all the determinations performed are that the accelerator 2 is emitting the charged particle beams K and R, in a case where the interlock 29 is operated, the emission determination unit 40 determines that the interlock 29 is prohibiting the accelerator 2 from emitting the charged particle beams K and R and automatic restoration is not possible. The time measurement unit 50 ends the measurement of the emission time in a case where the interlock 29 regulates emission of the charged particle beams K and R.

In a case where the emission determination unit 40 does not receive information indicating that automatic restoration is not possible from the interlock 29, the emission determination unit 40 determines the state of emission of the charged particle beams K and R from the accelerator 2 based on the above-described one or more determinations. The time measurement unit 50 continues the measurement of the emission time in a case where the interlock 29 does not regulate emission of the charged particle beams K and R.

The first control unit 60 controls the accelerator 2 based on the emission time measured by the time measurement unit 50. The first control unit 60 determines a scheduled emission time, for which the patient 100 is scheduled to be irradiated with the neutron ray N, based on a treatment plan with respect to the patient 100. In a case where the emission time measured by the time measurement unit 50 reaches the scheduled emission time, the first control unit 60 prohibits the accelerator 2 from emitting the charged particle beams K and R. After the first control unit 60 prohibits the accelerator 2 from emitting the charged particle beams K and R, the first control unit 60 ends the controlling of the accelerator 2. That is, as long as the emission time measured by the time measurement unit 50 does not reach the scheduled emission time, the first control unit 60 continues the controlling of the accelerator 2. Note that, the emission determination unit 40 determines whether or not the accelerator 2 is emitting the charged particle beams K and R while the first control unit 60 is controlling the accelerator 2.

The neutron capture therapy apparatus 1 includes a plurality of electronic control units 32 and 33 that control emission of the charged particle beam R in the accelerator 2. Each of the plurality electronic control units 32 and 33 has the same configuration as the electronic control unit 31, for example. The electronic control unit 32 includes the second control unit 70 that controls emission of the charged particle beam R in the accelerator 2. The electronic control unit 33 includes the second control unit 71 that controls emission of the charged particle beam R in the accelerator 2. The first control unit 60, the second control unit 70, and the second control unit 71 are electronic control units independent of each other, for example. The first control unit 60, the second control unit 70, and the second control unit 71 control the accelerator 2 independently of each other.

The second control unit 70 controls the accelerator 2 based on the amount of electrons measured by the foil stripper 27. The second control unit 70 determines, based on a treatment plan with respect to the patient 100, a scheduled output, which is a scheduled output at the time of irradiation with the neutron ray N is performed, and an allowable error range, which is an allowable error range with respect to the scheduled output, in advance. The second control unit 70 calculates an electron conversion output, which is the output of the neutron ray N, from the amount of electrons measured by the foil stripper 27.

In a case where the electron conversion output falls in the allowable error range with respect to the scheduled output, the second control unit 70 maintains emission of the charged particle beam R caused by the accelerator 2. In a case where the electron conversion output does not fall in the allowable error range with respect to the scheduled output, the second control unit 70 controls the accelerator 2 such that the electron conversion output falls in the allowable error range with respect to the scheduled output. The second control unit 70 prohibits the accelerator 2 from emitting the charged particle beams K and R in a case where the electron conversion output is maintained for a predetermined time, for example. The second control unit 70 ends the controlling of the accelerator 2 after prohibiting the accelerator 2 from emitting the charged particle beams K and R.

The second control unit 71 controls the accelerator 2 based on the result of measurement performed by the current monitor 5. The second control unit 71 calculates a current conversion output, which is the output of the neutron ray N, from the result of measurement performed by the current monitor 5.

In a case where the current conversion output falls in the allowable error range with respect to the scheduled output, the second control unit 71 maintains emission of the charged particle beam R caused by the accelerator 2. In a case where the current conversion output does not fall in the allowable error range with respect to the scheduled output, the second control unit 71 controls the accelerator 2 such that the current conversion output falls in the allowable error range with respect to the scheduled output. The second control unit 71 prohibits the accelerator 2 from emitting the charged particle beams K and R in a case where the current conversion output is maintained for a predetermined time, for example. The second control unit 71 ends the controlling of the accelerator 2 after prohibiting the accelerator 2 from emitting the charged particle beams K and R.

In a case where the second control unit 70 or the second control unit 71 prohibits emission of the charged particle beams K and R in the accelerator 2, the first control unit 60 causes the emission determination unit 40 to end the determination, causes the time measurement unit 50 to end the measurement of an emission time $T_0$, and ends the controlling of the accelerator 2.

Figure 2A:
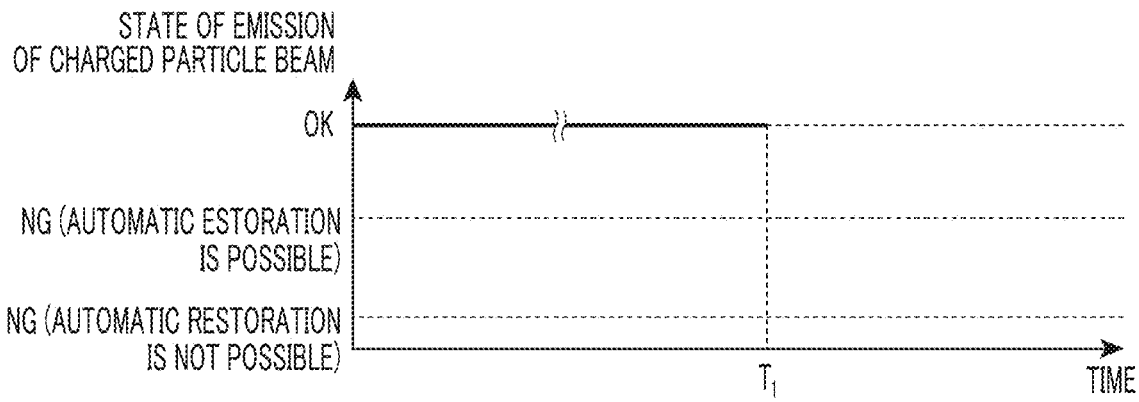
FIGS. 2A to 2C are graphs each showing the state of emission of a charged particle beam in the radiation treatment apparatus according to the embodiment.
Figure 2B:
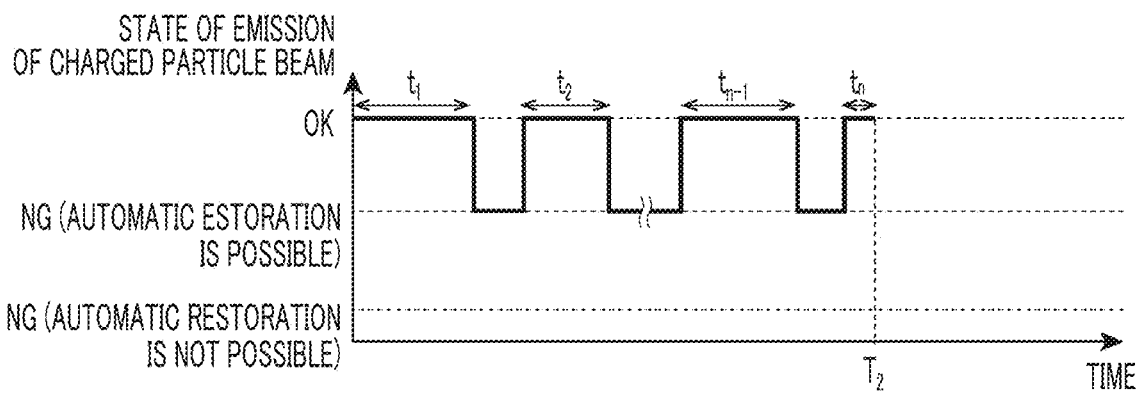
Figure 2C:
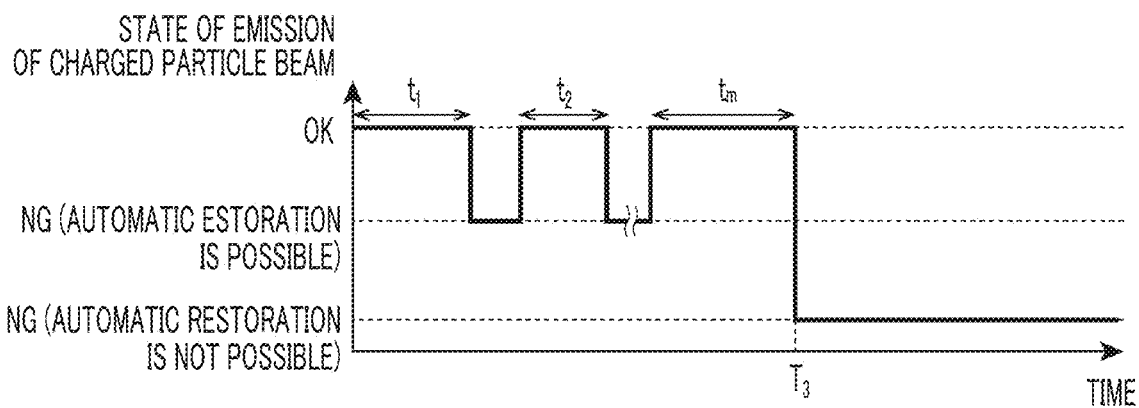

Next, a method of measuring an emission time by means of the time measurement unit 50 will be described. As shown in FIGS. 2A to 2C, the time measurement unit 50 measures an emission time. FIG. 2A shows a relationship between the state of emission of the charged particle beams K and R in the accelerator 2 and time which relates to a case where the emission determination unit 40 continuously determines that the accelerator 2 is emitting the charged particle beams K and R.

In a case where the emission determination unit 40 determines that the accelerator 2 is emitting the charged particle beams K and R ("OK" in FIGS. 2A to 2C), the time measurement unit 50 measures the emission time $T_0$ and adds up. In a case where the emission time $T_0$ measured by the time measurement unit 50 reaches a scheduled emission time $T_1$, the first control unit 60 ends emission of the charged particle beams K and R caused by the accelerator 2. The first control unit 60 ends the controlling of the accelerator 2. Accordingly, the emission determination unit 40 ends a determination on whether or not the accelerator 2 is emitting the charged particle beams K and R. Since the result of the determination performed by the emission determination unit 40 is not received, the time measurement unit 50 ends the measurement of the emission time $T_0$. Note that, the scheduled emission time $T_1$ is determined based on a treatment plan.

FIG. 2B shows a relationship between the state of emission of the charged particle beams K and R in the accelerator 2 and time which relates to a case where both of a case where the emission determination unit 40 determines that the accelerator 2 is emitting the charged particle beams K and R and a case where the emission determination unit 40 determines that the accelerator 2 is not emitting the charged particle beams K and R occur. FIG. 2B shows a case where the emission determination unit 40 determines that the accelerator 2 is not emitting the charged particle beams K and R n−1 times (n is integer equal to or greater than 2) until the emission time $T_0$ of the time measurement unit 50 reaches the scheduled emission time $T_1$.

First, in a case where the emission determination unit 40 determines that the accelerator 2 is emitting the charged particle beams K and R ("OK" in FIGS. 2A to 2C), the time measurement unit 50 continues measurement of the emission time $T_0$. In a case where the emission determination unit 40 determines that the accelerator 2 is not emitting the charged particle beams K and R ("NG (automatic restoration is possible)" in FIGS. 2A to 2C), the time measurement unit 50 temporarily stops measurement of the emission time $T_0$. In a case where the emission determination unit 40 continuously determines that the accelerator 2 is not emitting the charged particle beams K and R ("NG (automatic restoration is possible)" in FIGS. 2A to 2C), there is no change in emission time $T_0$ of the time measurement unit 50. In a case where the controller 30 performs automatic restoration and the emission determination unit 40 determines that the accelerator 2 is emitting the charged particle beams K and R ("OK" in FIGS. 2A to 2C), the time measurement unit 50 restarts the measurement of the emission time $T_0$.

When the number of times that measurement of the emission time $T_0$ is started with the time measurement unit 50 starting or restarting the measurement reaches p (p is integer equal to or greater than 1 and equal to or smaller than n), the time measurement unit 50 sets a time for which the result of a determination is that the accelerator is emitting the charged particle beams as a measured time $t_p$. The time measurement unit 50 adds up all of measured times ($t_1$, $t_2$, ... $t_{n-1}$, and $t_n$) to measure the total emission time $T_0$. That is, the time measurement unit 50 does not add a time, for which the result of the determination continuously performed by the emission determination unit 40 is that the accelerator 2 is not emitting the charged particle beams K and R, to the emission time $T_0$.

In a case where the measured emission time reaches the scheduled emission time $T_1$, the first control unit 60 ends emission of the charged particle beams K and R caused by the accelerator 2. The first control unit 60 ends the controlling of the accelerator 2. Accordingly, the emission determination unit 40 ends a determination on whether or not the accelerator 2 is emitting the charged particle beams K and R. Since the result of the determination performed by the emission determination unit 40 is not received, the time measurement unit 50 ends the measurement of the emission time $T_0$. Note that, even when a time $T_2$ between the start of measurement performed by the time measurement unit 50 and the end of the measurement exceeds the scheduled emission time $T_1$, the first control unit 60 does not end the controlling of the accelerator 2.

FIG. 2C shows a relationship between the state of emission of the charged particle beams K and R in the accelerator 2 and time which relates to a case where both of a case where the emission determination unit 40 determines that the accelerator 2 is emitting the charged particle beams K and R and a case where the emission determination unit 40 determines that the accelerator 2 is not emitting the charged particle beams K and R occur and the interlock 29 is operated. FIG. 2C shows a case where the emission determination unit 40 determines that the accelerator 2 is not emitting the charged particle beams K and R m−1 times (m is integer equal to or greater than 2) before the emission time $T_0$ of the time measurement unit 50 reaches the scheduled emission time $T_1$ and the interlock 29 is operated.

In a case where the emission determination unit 40 determines that the accelerator 2 is emitting the charged particle beams K and R ("OK" in FIGS. 2A to 2C), the time measurement unit 50 continues measurement of the emission time $T_0$. In a case where the emission determination unit 40 determines that the accelerator 2 is not emitting the charged particle beams K and R ("NG (automatic restoration is possible)" in FIGS. 2A to 2C), the time measurement unit 50 temporarily stops measurement of the emission time T0. In a case where the emission determination unit 40 continuously determines that the accelerator 2 is not emitting the charged particle beams K and R ("NG (automatic restoration is possible)" in FIGS. 2A to 2C), there is no change in emission time T0 of the time measurement unit 50. In a case where the controller 30 performs automatic restoration and the emission determination unit 40 determines that the accelerator 2 is emitting the charged particle beams K and R ("OK" in FIGS. 2A to 2C), the time measurement unit 50 restarts the measurement of the emission time $T_0$.

In a case where the emission determination unit 40 determines that the interlock 29 is prohibiting the accelerator 2 from emitting the charged particle beams K and R and automatic restoration is not possible ("NG (automatic restoration is not possible)" in FIGS. 2A to 2C), the time measurement unit 50 ends the measurement of the emission time $T_0$. Note that, the meaning of "to end measurement" is to end a control process itself which is performed by the electronic control unit 31 for measurement of the emission time $T_0$. Meanwhile, the meaning of "to temporarily stop measurement of the emission time $T_0$" is to continue the control process which is performed by the electronic control unit 31 for measurement of the emission time $T_0$ and to end measurement of the measured time only. At this time, in a case where automatic restoration is performed by the controller 30, measurement of the measured time is restarted immediately.

The time measurement unit 50 adds up all of measured times ($t_1$, $t_2$, $t_{m-1}$, and $t_m$) to measure the total emission time $T_0$. In a case where the measured emission time $T_0$ reaches the scheduled emission time $T_1$, the first control unit 60 ends the controlling of the accelerator 2. Even in a case where the interlock 29 is not operated with the measured emission time not reaching the scheduled emission time $T_1$, the first control unit 60 ends the controlling of the accelerator 2. Accordingly, the emission determination unit 40 ends a determination on whether or not the accelerator 2 is emitting the charged particle beams K and R. Since the result of the determination performed by the emission determination unit 40 is not received, the time measurement unit 50 ends the measurement of the emission time T0. Note that, regardless of whether or not a time $T_3$ between the start of measurement performed by the time measurement unit 50 and the end of the measurement is equal to or greater than the scheduled emission time $T_1$, the first control unit 60 ends the controlling of the accelerator 2 at a time point at which the interlock 29 is operated.

Figure 3:
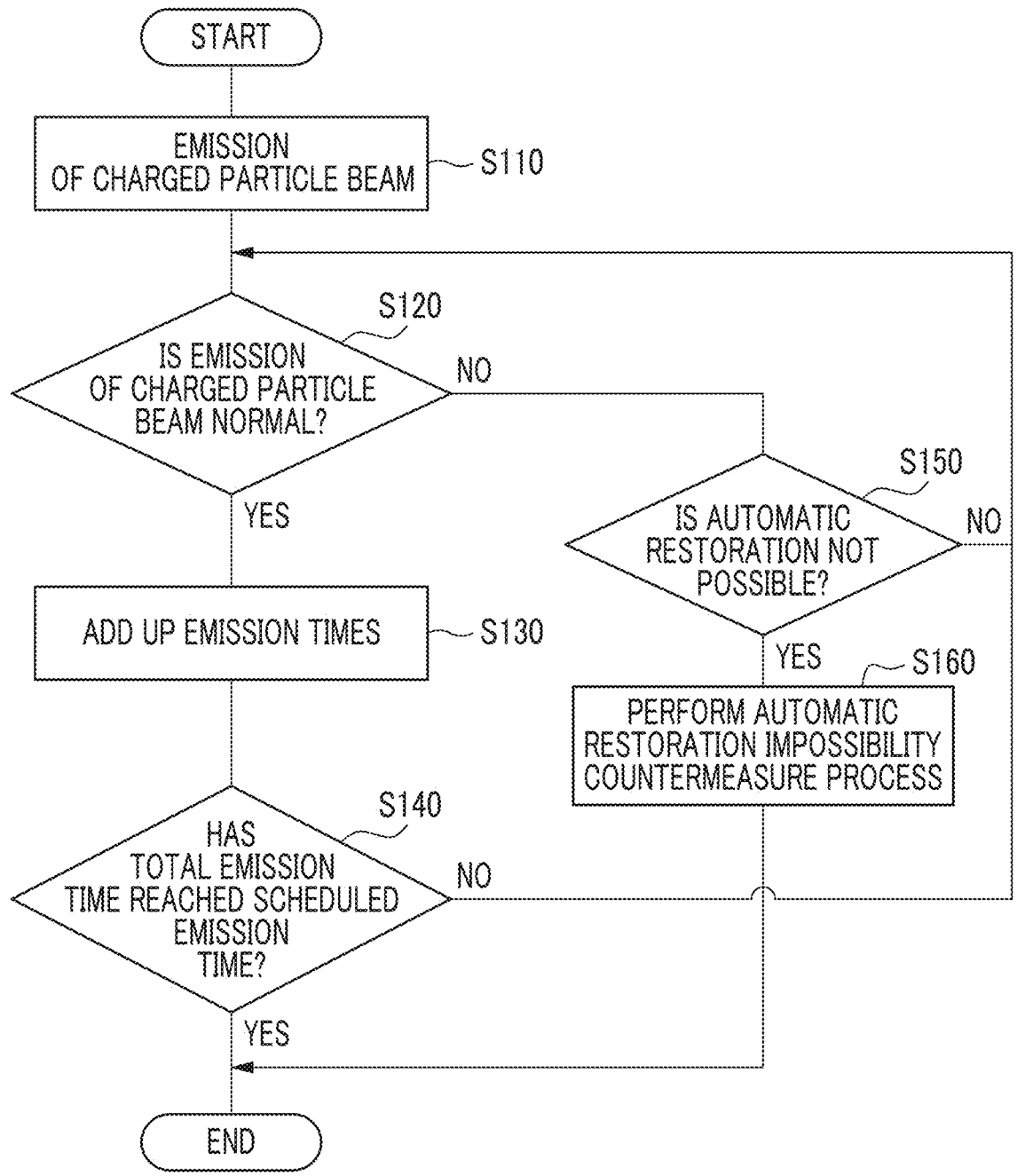
FIG. 3 is a flowchart showing an example of the controlling of the radiation treatment apparatus according to the embodiment.

Next, with reference to FIG. 3, the procedure for controlling the neutron capture therapy apparatus 1 in the embodiment will be described. First, the controller 30 causes the charged particle beams K and R to be emitted (step S110: emission start process). Next, the emission determination unit 40 determines whether or not emission of the charged particle beams K and R in the accelerator 2 is normal (step S120: emission determination process). In the emission determination unit 40, one or more determinations from among the determination based on the ion source information, the determination based on the high-frequency electric power information, and the determination based on the opening and closing information are used.

The emission determination unit 40 determines that emission of the charged particle beams K and R in the accelerator 2 is normal in a case where the results of all the determinations are that the accelerator 2 is emitting the charged particle beams K and R. That is, the emission determination unit 40 determines that the accelerator 2 is emitting the charged particle beams K and R. In this case, next, the time measurement unit 50 adds up emission times (step S130: adding-up process). The time measurement unit 50 adds the measured time $t_p$ to the emission time $T_0$.

That is, the emission determination unit 40 determines that emission of the charged particle beams K and R in the accelerator 2 is not normal in a case where the result of any one of the above-described determinations is that the accelerator 2 is not emitting the charged particle beams K and R. That is, the emission determination unit 40 determines that the accelerator 2 is not emitting the charged particle beams K and R. In this case, next, the emission determination unit 40 determines whether or not the state of emission of the charged particle beams K and R in the accelerator 2 is a state where automatic restoration is not possible (step S150: restoration determination process). In a case where the emission determination unit 40 determines that the state of emission of the charged particle beams K and R in the accelerator 2 is a state where the automatic restoration is not impossible (automatic restoration is possible), the emission determination unit 40, the time measurement unit 50, and the first control unit 60 perform a series of processes from the emission determination process (S120) again. At this time, the controller 30 performs automatic restoration of the neutron capture therapy apparatus 1.

In a case where the emission determination unit 40 determines that the state of emission of the charged particle beams K and R in the accelerator 2 is a state where the automatic restoration is not possible (automatic restoration is not possible) because of the interlock 29, the first control unit 60 performs an automatic restoration impossibility countermeasure process (step S160: automatic restoration impossibility countermeasure process). The first control unit 60 ends the controlling of the accelerator 2. The time measurement unit 50 ends measurement of the emission time $T_0$. In a case where the neutron capture therapy apparatus 1 is restarted by an operation performed by an operator or the like, the controller 30 starts from the emission start process (S110).

In a case where the adding-up process (S130) is performed by the time measurement unit 50, next, the first control unit 60 determines whether or not the total emission time $T_0$ has reached the scheduled emission time $T_1$ (step S140: completion determination process). In a case where the total emission time $T_0$ has not reached the scheduled emission time $T_1$, the emission determination unit 40, the time measurement unit 50, and the first control unit 60 perform a series of processes from the emission determination process (S120) again. In a case where the total emission time $T_0$ reaches the scheduled emission time $T_1$, the first control unit 60 ends emission of the charged particle beams K and R caused by the accelerator 2. The first control unit 60 ends the controlling of the accelerator 2. In this manner, the controlling of the neutron capture therapy apparatus 1 ends.

Next, the action and effect of the neutron capture therapy apparatus 1 in the embodiment will be described.

The neutron capture therapy apparatus 1 according to the embodiment includes the accelerator 2 that emits the charged particle beams K and R, the time measurement unit 50 that measures the emission time of the charged particle beams K and R of the accelerator 2, the first control unit 60 that controls the accelerator 2 based on the emission time $T_0$ measured by the time measurement unit 50, and the emission determination unit 40 that determines whether or not the accelerator 2 is emitting the charged particle beams K and R while the first control unit 60 is controlling the accelerator 2, and the time measurement unit 50 adds a time, for which the result of a determination performed by the emission determination unit 40 is that the accelerator 2 is emitting the charged particle beams K and R, to the emission time $T_0$ of the charged particle beams K and R of the accelerator 2 and does not add a time, for which the result of the determination performed by the emission determination unit 40 is that the accelerator 2 is not emitting the charged particle beams K and R, to the emission time $T_0$ of the charged particle beams K and R of the accelerator 2.

The neutron capture therapy apparatus 1 includes the time measurement unit 50 that adds a time, for which the result of a determination performed by the emission determination unit 40 is that the accelerator 2 is emitting the charged particle beams K and R, to the emission time $T_0$ of the charged particle beams K and R and the first control unit 60 that controls the accelerator 2 based on the emission time $T_0$ measured by the time measurement unit 50. According to such a configuration, the time, for which the result of the determination is that the accelerator 2 is not emitting the charged particle beams K and R, is not added to the emission time $T_0$ and thus the first control unit can perform control in accordance with the state of emission of the charged particle beams K and R. Accordingly, with the neutron capture therapy apparatus 1, it is possible to end emission of the charged particle beams K and R at an appropriate timing.

Since the length of treatment time in a neutron capture therapy is longer than other radiation treatment methods, there may be a time when the output of the charged particle beams K and R or the neutron ray N does not fit an output based on a treatment plan. That is, there is a time when emission of the charged particle beams K and R is temporarily stopped while a long treatment time elapses. In addition, in a case where a control system including a timer as in the related art is applied to the neutron capture therapy apparatus, a time that does not fit a treatment plan is also measured since the timer measures an elapsed time from the start of measurement. Therefore, there is a possibility that emission ends in a case where the elapsed time from the start of measurement reaches the scheduled emission time $T_1$ even in a case where the emission time of the charged particle beams K and R or the neutron ray N actually emitted at an appropriate output does not reach the scheduled emission time $T_1$ for which the emission needs to be performed.

According to the time measurement unit 50 of the neutron capture therapy apparatus 1 in the embodiment, it is possible to measure a time for which the charged particle beams K and R, of which the output is set to a necessary output fitting in a treatment plan, are emitted. Therefore, the first control unit 60 can end emission of the charged particle beams K and R at an appropriate time fitting the treatment plan, based on a time measured by the time measurement unit 50. Accordingly, even in the case of a neutron capture therapy in which a treatment time is longer than that of other radiation treatment methods, it is possible to emit the charged particle beams K and R or the neutron ray N only for a necessary time fitting a treatment plan and end the emission at a time fitting the treatment plan.

In the embodiment, the emission determination unit 40 may determine whether or not the charged particle beams K and R are being emitted based on a signal relating to generation of the charged particle beams K and R in the accelerator 2. The time measurement unit 50 can measure the emission time $T_0$ of the charged particle beams K and R through a determination that is performed based on the signal relating to the generation of the charged particle beams K and R in the emission determination unit 40. Accordingly, with the neutron capture therapy apparatus 1, it is possible to appropriately measure the emission time $T_0$ of the charged particle beams K and R.

In the embodiment, the accelerator 2 may include the ion source unit 22 that generates a charged particle and the emission determination unit 40 may determine whether or not the accelerator 2 is emitting the charged particle beams K and R based on ion source information of the ion source unit 22. The time measurement unit 50 can measure the emission time $T_0$ of the charged particle beams K and R through a determination that is performed based on the ion source information of the ion source unit 22 in the emission determination unit 40. Accordingly, with the neutron capture therapy apparatus 1, it is possible to appropriately measure the emission time $T_0$ of the charged particle beams K and R in the accelerator 2.

In the embodiment, the accelerator 2 may include the stopper 26 that is provided on the trajectory of the charged particle beam K and controls passage and blockage of the charged particle beam K by being opened and closed and the emission determination unit 40 may determine whether or not the accelerator 2 is emitting the charged particle beams K and R based on whether the stopper 26 is open or closed. The time measurement unit 50 can measure the emission time of the charged particle beams K and R through a determination that is performed based on whether the stopper 26 is open or closed in the emission determination unit 40. Accordingly, with the neutron capture therapy apparatus 1, it is possible to appropriately measure the emission time $T_0$ of the charged particle beams K and R in the accelerator 2 based on whether the stopper 26 is open or closed in the accelerator 2.

In the embodiment, the accelerator 2 may include the signal source 25 that outputs high-frequency electric power and the emission determination unit 40 may determine whether the accelerator 2 is emitting the charged particle beams K and R based on the high-frequency electric power. The time measurement unit 50 can measure the emission time $T_0$ of the charged particle beams K and R through a determination that is performed based on the high-frequency electric power of the signal source 25 in the emission determination unit 40. Accordingly, with the neutron capture therapy apparatus 1, it is possible to appropriately measure the emission time $T_0$ of the charged particle beams K and R in the accelerator 2 based on the high-frequency electric power of the signal source 25 in the accelerator 2.

In the embodiment, the beam duct 3 through which the charged particle beam R emitted from the accelerator 2 is transported, a plurality of signal measurement units (current monitor 5 and foil stripper 27) that are provided in the beam duct 3 and measure a signal of the charged particle beam R, and a plurality of the second control units 70 and 71 that control the accelerator 2 based on the result of measurement performed by the plurality of signal measurement units may be provided and the first control unit 60 and the plurality of second control units 70 and 71 may control the accelerator 2 independently of each other. In this case, the first control unit 60 and the plurality of second control units 70 and 71 can control the accelerator 2 based on the emission time $T_0$ in the time measurement unit 50 and the result of measurement in the plurality of signal measurement units. Since the first control unit and the plurality of second control units are independent of each other, with the neutron capture therapy apparatus 1, it is possible to end emission of the charged particle beam at an appropriate timing based on a plurality of conditions.

In the embodiment, the accelerator 2 may include the interlock 29 that regulates emission of the charged particle beams K and R and the first control unit 60 may control the accelerator 2 in a case where the interlock 29 regulates emission of the charged particle beams K and R and may not control the accelerator 2 in a case where the interlock 29 does not regulate emission of the charged particle beams K and R. In a case where the interlock 29 regulates emission of the charged particle beams K and R, it may take time to terminate the regulation. During the regulation performed by the interlock 29, the first control unit 60 does not control the accelerator 2 and thus the emission determination unit 40 does not determine whether or not the charged particle beams K and R are being emitted. Therefore, the time measurement unit 50 does not add up the emission time $T_0$ of the charged particle beams K and R. In a case where there is no regulation performed by the interlock 29, the first control unit 60 performs control based on the emission time $T_0$. Therefore, the first control unit 60 can suppress the end of a neutron ray capture therapy during the regulation performed by the interlock 29.

The invention is not limited to the above embodiments.

In a case where the emission determination unit 40 determines that the interlock 29 is prohibiting the accelerator 2 from emitting the charged particle beams K and R and automatic restoration is not possible ("NG (automatic restoration is not possible)" in FIGS. 2A to 2C), the time measurement unit 50 may stop measurement of the emission time $T_0$. In this case, the interlock 29 is released based on an operation performed by an operator or the like and in a case where restoration is performed, the time measurement unit 50 may restart measurement of the emission time $T_0$ and newly add the emission time $T_0$ after the restoration to the emission time $T_0$ before the restoration.

The time measurement unit 50 may measure times, for which the result of a determination continuously performed by the emission determination unit 40 is that the accelerator 2 is not emitting the charged particle beams K and R ("NG (automatic restoration is possible)" and "NG (automatic restoration is not possible)" in FIGS. 2A to 2C), as extension times. In this case, the time measurement unit 50 sequentially adds the measured extension times to the original scheduled emission time $T_1$ to update the scheduled emission time $T_1$. The time measurement unit 50 may end measurement at a time point at which an elapsed time after the start of the measurement reaches the updated scheduled emission time $T_1$.

In the embodiment, two types of control units have been described as the second control units 70 and 71. However, a configuration including three or more control units may also be adopted. The neutron capture therapy apparatus 1 may determine the state of emission of the charged particle beams K and R caused by the accelerator 2 based on the dose of the charged particle beam R calculated by the current monitor 5, the dose of a gamma ray calculated by the gamma ray detection unit 11, and the dose of the neutron ray N. The plurality of second control units may control the accelerator 2 independently of each other in a case where the dose of the charged particle beam R, the dose of the gamma ray, and the dose of the neutron ray N are lower than threshold values set for the dose of the charged particle beam R, the dose of the gamma ray, and the dose of the neutron ray N, respectively. Note that, the dose of the neutron ray N is measured by means of a scintillator, an optical fiber, a photodetector or the like in the collimator 10.

With respect to the time measurement unit 50, the second control unit 70 may transmit a timing at which an electron conversion output becomes out of an allowable error range with respect to a scheduled output and a timing at which the electron conversion output falls into the allowable error range with respect to the scheduled output to the time measurement unit 50. With respect to the time measurement unit 50, the second control unit 71 may transmit a timing at which a current conversion output becomes out of an allowable error range with respect to a scheduled output and a timing at which the current conversion output falls into the allowable error range with respect to the scheduled output to the time measurement unit 50. The time measurement unit 50 may measure the emission time $T_0$ based on the timings. For example, the time measurement unit 50 measures the emission time $T_0$ in a case where the results of all determinations in the emission determination unit 40 are that the charged particle beams K and R are being emitted from the accelerator 2 and the electron conversion output and the current conversion output fall in the allowable error ranges with respect to the scheduled outputs in the second control units 70 and 71.

The accelerator 2 in the neutron capture therapy apparatus 1 may be a linac. In this case, the accelerator 2 may include a drift tube linac (DTL). The emission determination unit 40 may include a DTL determination unit that determines whether or not the accelerator 2 is emitting the charged particle beams K and R based on energy information from a monitor of the DTL in addition to the ion source determination unit and the signal source determination unit. The DTL determination unit determines whether or not the accelerator 2 is emitting the charged particle beams K and R through comparison between a DTL threshold value, which is a threshold value determined in advance, and the energy information obtained from the monitor. In the emission determination unit 40, one or more determinations from among the determination based on the ion source information, the determination based on the high-frequency electric power information, and the determination based on the energy information are performed. In addition, as a monitor that is connected to the plurality of second control units and monitors the state of emission of the charged particle beam R, a current transformer (CT) (current sensor), a DCCT, an alternate current transformer (ACCT) (alternate current sensor), or the like is used.

The accelerator 2 of the neutron capture therapy apparatus 1 may be an electrostatic accelerator. In this case, as a monitor that is connected to the plurality of second control units and monitors the state of emission of the charged particle beam R, a DCCT, a nuclear fission monitoring device (fission monitor), a $^3$He proportional counter, an $H_2^+$ monitor, or the like is used.

The radiation treatment apparatus may not be the neutron capture therapy apparatus 1. The radiation treatment apparatus may be a proton beam treatment apparatus. The accelerator 2 of the proton beam treatment apparatus may be a synchrotron. The accelerator 2 includes an ion source unit, a linac, a main ring, and the like. The emission determination unit 40 performs one or more determinations from among determinations performed based on the state of operation of the ion source unit, the state of operation of the linac, the state of operation of the main ring, and whether or not a stopper in the accelerator 2 has been retracted. In addition, as a monitor that is connected to the plurality of second control units and monitors the state of emission of the charged particle beam R, an ionization chamber is used.

The accelerator 2 of the proton beam treatment apparatus may be a cyclotron. The accelerator 2 includes an ion source unit, a signal source, a chopper, and the like. The emission determination unit 40 performs one or more determinations from among determinations performed based on the state of operation of the ion source unit, the state of operation of the signal source, the state of operation of the chopper, and whether or nota stopper in the accelerator 2 has been retracted. In addition, as a monitor that is connected to the plurality of second control units and monitors the state of emission of the charged particle beam R, an ionization chamber is used.

It should be understood that the invention is not limited to the above-described embodiment, but may be modified into various forms on the basis of the spirit of the invention. Additionally, the modifications are included in the scope of the invention.

What is claimed is:

1. A radiation treatment apparatus comprising:
   an accelerator that emits a charged particle beam;
   a time measurement unit that measures an emission time of the charged particle beam of the accelerator;
   a first control unit that controls the accelerator based on the emission time measured by the time measurement unit; and
   an emission determination unit that determines whether or not the accelerator is emitting the charged particle beam while the first control unit is controlling the accelerator,
   wherein the time measurement unit adds a time, for which a result of a determination performed by the emission determination unit is that the accelerator is emitting the charged particle beam, to the emission time of the charged particle beam of the accelerator and does not add a time, for which the result of the determination performed by the emission determination unit is that the accelerator is not emitting the charged particle beam, to the emission time of the charged particle beam of the accelerator.

2. The radiation treatment apparatus according to claim 1, wherein the emission determination unit determines whether or not the charged particle beam is being emitted based on information indicating a state of generation of the charged particle beam in the accelerator.

3. The radiation treatment apparatus according to claim 2, wherein the accelerator includes a generation source that generates a charged particle, and
   wherein the emission determination unit determines whether or not the accelerator is emitting the charged particle beam based on information indicating a state of generation of the charged particle at the generation source.

4. The radiation treatment apparatus according to claim 2, wherein the accelerator includes a stopper that is provided on a trajectory of the charged particle beam and controls passage and blockage of the charged particle beam by being opened and closed, and
   wherein the emission determination unit determines whether or not the accelerator is emitting the charged particle beam based on information indicating an opening and closing state of the stopper.

5. The radiation treatment apparatus according to claim 2, wherein the accelerator includes a signal source that outputs high-frequency electric power, and
   wherein the emission determination unit determines whether or not the accelerator is emitting the charged particle beam based on information indicating a state of the high-frequency electric power.

6. The radiation treatment apparatus according to claim 1, further comprising:
   a plurality of charged particle beam measurement units that are provided in a beam path of the charged particle beam and measure a state of the charged particle beam; and
   a plurality of second control units that control the accelerator based on a result of measurement performed by the plurality of charged particle beam measurement units,
   wherein the first control unit and the plurality of second control units control the accelerator independently of each other.

7. The radiation treatment apparatus according to claim 1,
wherein the accelerator includes an interlock that regulates emission of the charged particle beam, and
wherein the time measurement unit continues measurement of the emission time in a case where the interlock does not regulate the emission of the charged particle beam and ends the measurement of the emission time in a case where the interlock regulates the emission of the charged particle beam.

\* \* \* \* \*